US011987623B2

(12) United States Patent
Günther et al.

(10) Patent No.: US 11,987,623 B2
(45) Date of Patent: *May 21, 2024

(54) STABILIZED ANTIBODY COMPOSITIONS

(71) Applicant: NOVALIQ GMBH, Heidelberg (DE)

(72) Inventors: Bernhard Günther, Dossenheim (DE); Dieter Scherer, Laufen (CH); Anthony Pettigrew, Heidelberg (DE); Gesche Graf, Bensheim (DE)

(73) Assignee: NOVALIQ GMBH, Heidelberg (DE)

( * ) Notice: Subject to any disclaimer, the term of this patent is extended or adjusted under 35 U.S.C. 154(b) by 260 days.

This patent is subject to a terminal disclaimer.

(21) Appl. No.: 17/320,693

(22) Filed: May 14, 2021

(65) Prior Publication Data

US 2021/0340248 A1 Nov. 4, 2021

Related U.S. Application Data

(60) Continuation of application No. 16/294,506, filed on Mar. 6, 2019, now abandoned, which is a division of application No. 14/907,254, filed as application No. PCT/EP2014/065840 on Jul. 23, 2014, now Pat. No. 10,273,298.

(30) Foreign Application Priority Data

Jul. 23, 2013 (EP) ..................................... 13177699

(51) Int. Cl.
*A61K 39/395* (2006.01)
*C07K 16/28* (2006.01)

(52) U.S. Cl.
CPC ............ *C07K 16/28* (2013.01); *A61K 39/395* (2013.01); *A61K 39/39591* (2013.01); *C07K 2317/21* (2013.01); *C07K 2317/24* (2013.01); *C07K 2317/55* (2013.01); *C07K 2317/569* (2013.01); *C07K 2317/622* (2013.01); *C07K 2317/626* (2013.01); *C07K 2317/76* (2013.01); *C07K 2317/94* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 2,616,927 A | 11/1952 | Kauck et al. |
| 4,452,818 A | 6/1984 | Haidt |
| 5,077,036 A | 12/1991 | Long |
| 5,326,566 A | 7/1994 | Parab |
| 5,336,175 A | 8/1994 | Mames |
| 5,518,731 A | 5/1996 | Meadows |
| 5,667,809 A | 9/1997 | Trevino et al. |
| 5,874,469 A | 2/1999 | Maniar et al. |
| 5,874,481 A | 2/1999 | Weers et al. |
| 5,904,933 A | 5/1999 | Riess et al. |
| 5,980,936 A | 11/1999 | Krafft et al. |
| 5,981,607 A | 11/1999 | Ding |
| 6,042,845 A | 3/2000 | Sun et al. |
| 6,113,919 A | 9/2000 | Reiss et al. |
| 6,140,374 A | 10/2000 | May et al. |
| 6,159,977 A | 12/2000 | Reeves |
| 6,177,477 B1 | 1/2001 | George et al. |
| 6,197,323 B1 | 3/2001 | Georgieff |
| 6,224,887 B1 | 5/2001 | Samour et al. |
| 6,262,126 B1 | 7/2001 | Meinert |
| 6,294,563 B1 | 9/2001 | Garst |
| 6,372,243 B2 | 4/2002 | Kobuch |
| 6,391,879 B1 | 5/2002 | Reeves |
| 6,399,087 B1 | 6/2002 | Zhang et al. |
| 6,458,376 B1 | 10/2002 | Meadows |
| 6,486,212 B2 | 11/2002 | Meinert |
| 6,489,367 B1 | 12/2002 | Meinert |
| 6,730,328 B2 | 5/2004 | Maskiewicz et al. |
| 7,001,607 B1 | 2/2006 | Menz et al. |
| 7,026,359 B1 | 4/2006 | Gross |
| 7,258,869 B1 | 8/2007 | Berry et al. |
| 7,608,261 B2 | 10/2009 | Furfine et al. |
| 7,687,455 B2 | 3/2010 | Bonnet et al. |
| 7,740,875 B2 | 6/2010 | Dechow |
| 7,776,349 B2 | 8/2010 | Dechow |
| 8,029,977 B2 | 10/2011 | Meinert |
| 8,470,873 B2 | 6/2013 | Chen |
| 8,614,178 B2 | 12/2013 | Theisinger et al. |
| 8,759,404 B2 | 6/2014 | Daftary et al. |
| 8,796,340 B2 | 8/2014 | Theisinger et al. |
| 8,916,157 B2 | 12/2014 | Krause |
| 8,986,738 B2 | 3/2015 | Meinert |

(Continued)

FOREIGN PATENT DOCUMENTS

| | | |
|---|---|---|
| CN | 103096934 A | 5/2013 |
| EP | 0 670 159 A1 | 9/1995 |

(Continued)

OTHER PUBLICATIONS

Bardin et al., "Long-Range Nanometer-Scale Organization of SemifluorinatedAlkane Monolayers at the Air/Water Interface," Langmuir, 2011, 27, 13497-13505.
Broniatowski, M. et al., "Langmuir Monolayers Characteristics of Perfluorodecyl)—Alkanes, " Journal of Physical Chemistry B, 2004, 108, 13403-13411.
Costa Gomes et al., "Solubility of dioxygen in seven fluorinated liquids," Journal of Fluorine Chemistry, 2004, 125, 1325-1329.
Davies, N., "Biopharmaceutical Considerations in Topical Ocular Drug Delivery," Clinical and Experimental Pharmacology and Physiology, 2000, 27, 558-562.
Dembinski, R. et al., "Semi-fluorinated Alkanes as Carriers for Drug Targeting in Acute Respiratory Failure," Experimental Lung Research, 2010, 36, 499-507.
Dias et al., "Solubility of oxygen in liquid perfluorocarbons," Fluid PhaseEquilibria, 2004, 222-223:325-330.

(Continued)

*Primary Examiner* — Yunsoo Kim
(74) *Attorney, Agent, or Firm* — Hoxie & Associates LLC

(57) ABSTRACT

The invention provides novel compositions of antibodies based on liquid vehicles selected from semifluorinated alkanes. The use of these vehicles provides for improved stability and shelf-life of antibodies and their derivatives. The compositions are useful for topical administration or for parenteral injection.

20 Claims, 2 Drawing Sheets

(56) References Cited

U.S. PATENT DOCUMENTS

| | | |
|---|---|---|
| 9,005,626 B2 | 4/2015 | Seigfried |
| 9,241,900 B2 | 1/2016 | Wilson |
| 9,308,262 B2 | 4/2016 | Gunther et al. |
| 9,757,459 B2 | 9/2017 | Theisinger et al. |
| 9,757,460 B2 | 9/2017 | Gunther et al. |
| 9,770,508 B2 | 9/2017 | Gunther et al. |
| 9,968,678 B2 | 5/2018 | Theisinger et al. |
| 10,045,996 B2 | 8/2018 | Theisinger et al. |
| 10,058,615 B2 | 8/2018 | Günther et al. |
| 10,130,707 B2 | 11/2018 | Gunther et al. |
| 10,273,298 B2 | 4/2019 | Günther et al. |
| 10,369,117 B2 | 8/2019 | Gunther et al. |
| 10,449,164 B2 | 10/2019 | Günther et al. |
| 10,576,154 B2 | 3/2020 | Günther et al. |
| 10,682,315 B2 | 6/2020 | Scherer et al. |
| 10,813,976 B2 | 10/2020 | Löscher et al. |
| 11,160,865 B2 | 11/2021 | Theisinger et al. |
| 11,357,738 B2 | 6/2022 | Meinert |
| 2002/0006442 A1 | 1/2002 | Mishra et al. |
| 2002/0128527 A1 | 9/2002 | Meinert |
| 2002/0198266 A1 | 12/2002 | Meinert |
| 2003/0018044 A1 | 1/2003 | Pevman |
| 2003/0027833 A1 | 2/2003 | Cleary et al. |
| 2004/0265362 A1 | 12/2004 | Susilo |
| 2004/0266702 A1 | 12/2004 | Dawson et al. |
| 2005/0075407 A1 | 4/2005 | Tamarkin et al. |
| 2005/0079210 A1 | 4/2005 | Gupta |
| 2005/0175541 A1 | 8/2005 | Lanza et al. |
| 2005/0288196 A1 | 12/2005 | Horn |
| 2006/0009522 A1 | 1/2006 | Dana et al. |
| 2006/0013820 A1 | 1/2006 | Bonnet et al. |
| 2008/0019926 A1 | 1/2008 | Krafft et al. |
| 2008/0089923 A1 | 4/2008 | Burkstrand et al. |
| 2008/0207537 A1 | 8/2008 | Turner et al. |
| 2008/0234389 A1 | 9/2008 | Mecozzi et al. |
| 2010/0008996 A1 | 1/2010 | Meinert |
| 2010/0189765 A1 | 7/2010 | Erickson et al. |
| 2010/0226997 A1 | 9/2010 | Bowman et al. |
| 2010/0274215 A1 | 10/2010 | Wong et al. |
| 2011/0223208 A1 | 9/2011 | Hill et al. |
| 2012/0010280 A1 | 1/2012 | Aleo et al. |
| 2012/0095097 A1 | 4/2012 | Tabuchi et al. |
| 2012/0238639 A1 | 9/2012 | Theisinger et al. |
| 2013/0046014 A1 | 2/2013 | Theisinger |
| 2013/0084250 A1 | 4/2013 | Hagedorn et al. |
| 2013/0266652 A1 | 10/2013 | Theisinger et al. |
| 2013/0309226 A1 | 11/2013 | Armstrong et al. |
| 2014/0004197 A1 | 1/2014 | Theisinger et al. |
| 2014/0100180 A1 | 4/2014 | Gunther et al. |
| 2014/0140942 A1 | 5/2014 | Gunther et al. |
| 2014/0186350 A1 | 7/2014 | Ghosh et al. |
| 2016/0000941 A1 | 1/2016 | Keller et al. |
| 2016/0159902 A1 | 6/2016 | Günther et al. |
| 2017/0087100 A1 | 3/2017 | Scherer et al. |
| 2017/0087101 A1 | 3/2017 | Scherer et al. |
| 2017/0182060 A1 | 6/2017 | Wiedersberg et al. |
| 2018/0360908 A1 | 12/2018 | Beier et al. |
| 2019/0000919 A1 | 1/2019 | Brockmeyer et al. |
| 2019/0256591 A1 | 8/2019 | Günther et al. |
| 2019/0274970 A1 | 9/2019 | Günther et al. |
| 2019/0298801 A1 | 10/2019 | Kerwin et al. |
| 2019/0328717 A1 | 10/2019 | Günther et al. |
| 2019/0343793 A1 | 11/2019 | Günther et al. |
| 2020/0246463 A1 | 8/2020 | Günther et al. |
| 2021/0315832 A1 | 10/2021 | Scherer et al. |
| 2021/0340248 A1 | 11/2021 | Günther et al. |
| 2022/0143137 A1 | 5/2022 | Witt et al. |
| 2022/0354786 A1 | 11/2022 | Friess et al. |

FOREIGN PATENT DOCUMENTS

| | | |
|---|---|---|
| EP | 0 965 329 | 12/1999 |
| EP | 0 965 334 | 12/1999 |
| EP | 1 152 749 B1 | 4/2006 |
| JP | S6452722 | 2/1989 |
| JP | 2001/158734 | 6/2001 |
| JP | 2011/006348 | 1/2011 |
| WO | WO 96/40052 | 12/1996 |
| WO | WO 97/12852 | 4/1997 |
| WO | WO 1998/005301 | 2/1998 |
| WO | WO 2000/054588 | 9/2000 |
| WO | WO 2007/149334 | 12/2007 |
| WO | WO 2010/146536 | 12/2010 |
| WO | WO 2012/121754 | 9/2012 |
| WO | WO 2014/154531 | 10/2014 |
| WO | WO 2016/208989 | 6/2016 |
| WO | WO 2017/120601 | 7/2017 |

OTHER PUBLICATIONS

English-language machine translation of EP0670159 (A1) issued in U.S. Appl. No. 14/122,025, filed Apr. 1, 2015, 10 pages.

Freiburger Dokumentenserver (FreiDok), Albert-Ludwigs-Unversitat Freiburg, retrieved from http://www.freidok.uni-freiburg.de/volltexte/5682/, retrieved on Feb. 5, 2014, 2 pages.

Gerdenitsch, "Emulsions—established and promising drug carriers for parenteral adminstration", International Pharmaceutical Industry, 62-63, retrieved from internet: http://ipimediaworld.com/wp-content/uploads/2012/05/Pages-from-IPI-vol. 2-Issue-1-11.pdf Date Accessed: Jun. 20, 2016.

Griffin, W., "Classification of Surface-Active Agents by 'HLB'," Journal of the Society of Cosmetic Chemists, 1949, 1, 311-326.

Guirakhoo et al., "Cloning, expression and functional activities of a single chain antibody fragment directed to fusion protein of respiratory syncytial virus" Immunotechnology 2(3): 219-228 (Sep. 1996) Abstract Only.

Hardung, H., "Semifluorierte und perfluorierte Verbindungen zur topischen und parenteralen Anwendung," 2008, retrieved from http://www.freidok.uni-freiburg.de/volltexte/5682/pdf/Dissertation_Hardung.pdf [retrieved on Oct. 10, 2011].

Hardung, H., "Semifluorierte und perfluorierte Verbindungen zur topischenund parenteralen Anwendung," 2008, English Language Abstract, 2 pages, retrieved from https://freidok.uni-freiburg.de/data/5682 [retrieved on Jul. 10, 2017].

He et al., "High-throughput dynamic light scattering method for measuring viscosity of concentrated protein solutions" Analytical Biochemistry 399(1 ): 141-143 (Apr. 2010) Abstract Only.

Hoerauf, H. et al., "Combined Use of Partially Fluorinated Alkanes, Perfluorocarbon Liquids and Silicone Oil: An Experimental Study," Graefe's Archive for Clinical and Experimental Ophthalmology, 2001, 239 (5), 373-381.

Holm, R. et al., "A novel excipient, 1-perfluorohexyloctane shows limited utility for the oral delivery of poorly water-soluble drugs, " European Journal ofPharmaceutical Sciences, 2011, 42, 416-422.

JPS6452722, English Machine Translation of the Abstract, Description, andClaims, Espacenet, Date Accessed: Feb. 10, 2016, 4 pages.

Kaercher et al., "NovaTears® as new Therapy in Dry Eye Results from three prospective, multicenter, non-interventional studies in different patient populations," TFOS Conference (Tear Film & Ocular Surface), Sep. 7-10, 2016, Montpellier, France, Poster Session II, Poster No. 60, 1 page.

Knepp, V. et al., "Stability of Nonaqueous Suspension Formulations of PlasmaDerived Factor IX and Recombinant Human Alpha Interferon at Elevated Temperatures," Pharmaceutical Research, 1998, 15 (7), 1090-1095.

Kociok et al., "Influence on membrane-mediated cell activation by vesicles of silicone oil or perfluorohexyloctane," Graefe's Archive for Clinical and Experimental Ophthalmology 243(4): 345-358 (Apr. 2005) Abstract Only.

Mackiewicz, J. et al., "In Vivo Retinal Tolerance of Various Heavy Silicone Oils," Investigative Ophthalmology & Visual Science, 2007, 48 (4), 1873-1883.

Meinert, H. et al., "Semifluorinated Alkanes—A New Class of Compoundswith Outstanding Properties for Use in Ophthalmology," European Journal of Ophthalmology, 2000, 10 (3), 189-197.

Meinert, H. et al., "The Use of Semifluorinated Alkanes in Blood-Substitutes," Biomaterials, Artificial Cells, and Immobilization Biotechnology, 1993, 21 (5), 583-595.

(56) References Cited

OTHER PUBLICATIONS

Messmer et al. "Semifluorierte Alkane als Therapie bei Meibomdriisen-Dysfunktion Ergebnisse einer prospektiven, multizentrischen Beobachtungsstudie", Presentation, DOG-Kongress, Sep. 29-Oct. 2, 2016, Berlin DOG (Deutsche Ophtalmologische Gesellschaft), Poster No. PSa03-02, 1 page (German language version).

Messmer et al. "Semifluorinated Alkanes as a Therapy for Meibomian Gland Dysfunction Results of a prospective, multi-centered observational study", Presentation, DOG-Kongress, Sep. 29, 2016-Oct. 2, 2016, Berlin DOG (Deutsche Ophtalmologische Gesellschaft), Poster No. PSa03-02, English Translation, 6 pages.

Rosenberg, A., "Effects of Protein Aggregates: An Immunologic Perspective," The AAPS Journal, 2006, 8 (3), E501-E507.

Schmutz et al., "Fluorinated Vesicles Made from Combinations of Phospholipids and Semifluorinated Alkanes. Direct Experimental Evidence of the Location of the Semifluorinated Alkane within the Bilayer," Langmuir, 2003, 19:4889-4894.

Stevenson, C., "Characterization of Protein and Peptide Stability and Solubility in Non-Aqueous Solvents," Current Pharmaceutical Biotechnology, 2000, 1, 165-182.

Wang, W., "Lyophilization and Development of Solid Protein Pharmaceuticals," International Journal of Pharmaceutics, 2000, 203, 1-60.

Wong, D. et al., "Perfluorocarbons and Semifluorinated Alkanes," Seminars in Ophthalmology, 2000, 15 (1), 25-35.

Zhang et al., "Surface micelles of semifluorinated alkanes in Langmuir-Blodgett monolayers," Phys. Chem. Chem. Phys., 2004, 6:1566-1569.

Gehlsen et al., "A semifluorinated alkane (F4H5) as novel carrier for cyclosporine A: a promising therapeutic and prophylactic option for topical treatment of dry eye," Graefe's Arch. Clin. Exp. Ophthalmol., (2017) 255(4):767-775.

Gehlsen. U., et al., "Cyclosporine A using F4H5 as liquid drug carrier is effective in treating experimental dry-eye disease," Investigative Ophthalmology & Visual Science, 2015, 56(7):319, Abstract Only (2 pages).

Gehlsen, U., et al., "Omega-3 Fatty Acids Using F6H8-Carrier as Topical Therapy in Experimental Dry-Eye Disease," Investigative Ophthalmology & Visual Science, 2016, 57:417, Abstract Only (1 page).

Novaliq GmbH Begins Phase II Clinical Trial of Cyclasol for the Treatment of Moderate to Severe Dry Eye Disease, (online), 5 pages, (2016); retrieved on Jan. 8, 2021 from the Internet: https://www.biospace.com/article/releases/novaliq-gmbh-begins-phase-ii-clinical-trial-of-cyclasol-for-the-treatment-of-moderate-to-severe-dry-eye-disease-/.

Scherer et al., "Eyesol: A Novel Topical Ocular Drug Delivery System for Poorly Soluble Drugs," Drug Development & Delivery, vol. 13, No. 1, pp. 40-44, (2013).

Steven, P. et al. "Semifluorinated Alkane Eye Drops for Treatment of Dry Eye Disease—A Prospective, Multicenter Noninterventional Study" Journal of Ocular Pharmacology and Therapeutics, 2015, 31(8):498-503.

Steven et al., "Semifluorinated Alkane Eye Drops for Treatment of Dry Eye Disease Due to Meibomian Gland Disease," Journal of Ocular Pharmacology and Therapeutics, 2017, 33(9):1-8.

Wirta, David L. et al., "A Clinical Phase II Study to Assess Efficacy, Safety and Tolerability of Waterfree Cyclosporine Formulation for the Treatment of Dry Eye Disease," *Ophthalmology* 126:792-800 (2019).

STABILIZED ANTIBODY COMPOSITIONS

CROSS REFERENCE TO RELATED APPLICATIONS

This application is a continuation application of U.S. application Ser. No. 16/294,506, filed on Mar. 6, 2019, which is a divisional application of U.S. application Ser. No. 14/907,254, filed on Jan. 22, 2016, now U.S. Pat. No. 10,273,298, which is a United States Application filed under 35 U.S.C. § 371 claiming priority to and the benefit of PCT Application No. PCT/EP2014/065840, filed on Jul. 23, 2014, which claims the benefit of European Patent Application 13177699.9, filed on Jul. 23, 2013, the contents of each of which are hereby incorporated by reference in their entireties.

FIELD

The present invention is in the field of antibody compositions, in particular compositions which are useful as pharmaceutical formulations for therapeutic or diagnostic use.

BACKGROUND

Antibody-based therapies have come to the forefront in recent years as effective treatment options for numerous diseases such as cancer or autoimmune diseases, in conjunction with many new developments in antibody engineering and production technologies.

One of the major challenges associated with antibody formulation and delivery is maintaining the stability and form of the antibody therapeutic, in particular for long-term storage and for transport. Antibodies, like other types of protein-based therapeutics, are susceptible to physical and chemical instability under stress conditions such as temperature changes from freeze-thawing or during transport, exposure to light, oxygen or chemical/solvents, shear stress, and pH stress.

They may undergo denaturation (e.g. loss of tertiary and/or secondary structure) or interact to form aggregates. While antibody aggregation can occur in both the liquid and solid state, it is especially problematic in liquid formulations, especially at high concentrations of antibody. Antibodies are typically therapeutically effective at relatively high doses. High antibody concentrations, such as to minimize dose volumes and to make administration more patient-friendly (e.g. subcutaneous injection instead of intravenous infusion, decreased number of injections) are therefore generally desirable in pharmaceutical formulations.

Aggregation, in effect, can lead to loss of active antibody therapeutic, leading to unreliable and ineffective dosing. More significantly, aggregates may also exhibit toxicity and trigger undesirable or serious immunogenic responses. Aggregation resulting in the precipitation of large particulates which impede flow is undesirable for any kind of parenteral application.

Antibody modification and degradation via chemical pathways such as oxidation, deamidation, isomerization, disulfide bond formation and other irreversible crosslinking reactions may also occur over time and lead to inactivation of the antibody, as well as trigger aggregation. These reactions, along with aggregation, are often accelerated at elevated temperatures; refrigeration is consequently almost always a prerequisite. In many of these chemical reactions, water also plays a significant role either as a mediator or as a reactive intermediate such as in the hydrolytic cleavage of amide bonds. The exclusion of water, such as by lyophilization, or freeze-drying, to form a solid-state powder formulation may thus be an effective measure towards preparing a stable formulation of an antibody therapeutic.

Some of the formulations of marketed therapeutic antibody or antibody derivatives/fragments are based on lyophilized powder formulations which need to be reconstituted under sterile conditions with aqueous media shortly prior to administration by a trained medical or paramedical practitioner. For example, omalizumab (e.g. Xolair®, marketed by Genentech) is available as a lyophilized powder in a single-use vial.

The reconstitution of the lyophilized antibody in sterile aqueous media as an extra step prior to actual administration, however, carries the risk of improper handling (e.g. shaking) or dosing, as well as contamination. The reconstitution step itself may trigger aggregation if the pH or temperature of the aqueous medium is suboptimal, the time allowed for rehydration is too short or the vial is too aggressively shaken during the dissolving step. The propensity for waste is also higher, as failure to properly dissolve the lyophilized antibody product within the recommended time period usually requires for the sample to be discarded.

It should be noted that the lyophilization process step itself may induce aggregation and/or degradation. Additional stabilizing excipients such as saccharides or polyols are often added to the pre-lyophilization composition, along with other excipients such as bulking agents. The addition of other excipients may also be required after lyophilization in order to support the longer shelf-life of the antibody, adding to the number of components in the final formulation.

Ready-to-use liquid formulations would generally be preferred by the users, due to the ease of preparation for administration. If stable, a liquid formulation is also attractive for the pharmaceutical manufacturer due to the avoidance of lyophilisation, which is time-consuming and costly both during drug development and routine manufacture. Indeed, many marketed formulations of antibodies or antibody derivatives are aqueous-based solutions. With aqueous formulations, the pH of the medium can have a significant impact on the stability of the antibody in terms of promoting or reducing the likelihood of various degradative chemical reactions. Consequently, an optimized buffering system is always required, along with other formulation excipients such as antioxidant free-radical scavengers, surfactants and other anti-aggregation additives, or preservatives in order to provide stabilization to the antibody and counteract the various possible degradation processes that may occur during storage in an aqueous environment over time.

Alternative formulation options to lyophilization and aqueous solutions are also known, such as the use of non-aqueous liquids as carrier vehicles. For example, WO2012/121754 describes non-aqueous, high concentration suspension formulations comprising a hydrophobic vehicle such as sesame oil, and a viscosity-reducing agent such as ethyl oleate, and an anti-TNFα antibody. These compositions require addition of a viscosity-reducing agent that is fully miscible in the carrier, in order to make the oil carriers more amenable towards injection. Generally, the parenteral use of lipids and oils can cause pain and other undesirable side effects at the injection site. These types of compounds may also slow down the release of therapeutic agent, and are not ideal if rapid or immediate bioavailable is preferred.

Perfluorinated compounds have also been described as possible non-aqueous liquid carriers of biologically active agents such as proteins and peptides. For example, U.S. Pat.

No. 6,458,376 describes compositions proposed for ophthalmic applications (such as topically applied eye drops) in which therapeutic/diagnostic compounds, including oligopeptides and protein growth factors are suspended in perfluorocarbons or fluorinated silicone oils and in the presence of at least one surfactant. There is no mention, however, of such compositions comprising antibodies or antibody fragments and derivatives.

U.S. Pat. No. 6,730,328 describes thermally stable formulations in which non-aqueous, hydrophobic, non-reactive vehicles such as mineral oil, perfluorodecalin, methoxyflurane, perfluorotributylamine and tetradecane are used for suspension compositions comprising proteins, proteinaceous compounds and nucleic acids. The formulations are proposed for parenteral, transdermal, mucosal, oral and enteral methods of administration, as well as their use for long-term continuous administration and delivery via an implantable device. However, no specific example of a suspension of an antibody or antibody fragment or derivative in such vehicles is disclosed, nor is there any teaching with regard to the stability of such compositions at elevated temperatures beyond a three month time point. The actual tissue compatibility of these types of compositions has not been demonstrated either.

WO 2011/073134 discloses solutions of ciclosporin, a cyclic polypeptide with a molecular weight of 1202.31 in a semifluorinated alkane, optionally in the presence of a cosolvent such as ethanol. Whilst suspensions and emulsions are mentioned as optional alternatives, there is no specific disclosure of such type of composition, or any composition comprising high molecular weight proteinaceous species in the kiloDalton range such as antibodies or antibody fragments or derivatives.

It is therefore an object of the present invention to introduce novel antibody compositions which overcome any of the limitations and disadvantages associated with formulations currently known in the art.

SUMMARY OF THE INVENTION

In a first aspect, the invention provides a novel composition of an antigen-binding polypeptide or protein, and a liquid vehicle which comprises a semifluorinated alkane of the formula RFRH, wherein RF is a linear perfluorinated hydrocarbon segment with 4 to 12 carbon atoms, and wherein RH is a linear alkyl group with 4 to 8 carbons. The antigen-binding polypeptide or protein is incorporated in the composition such as to form a dispersion or suspension.

In another aspect, the antigen-binding polypeptide or protein may be selected from a monoclonal antibody, an antibody fragment, a polyclonal antibody, a fusion protein comprising an antibody fragment, or an antibody-drug conjugate.

In a further aspect, the invention provides a method for the treatment, prevention or diagnosis of a disease or condition in a patient in need thereof, comprising the step of administering a composition comprising an antigen-binding polypeptide or protein, and a liquid vehicle which comprises a semifluorinated alkane of the formula RFRH, wherein RF is a linear perfluorinated hydrocarbon segment with 4 to 12 carbon atoms, and wherein RH is a linear alkyl group with 4 to 8 carbons, and wherein the antigen-binding polypeptide or protein is incorporated in the composition such as to form a dispersion or suspension.

In yet another embodiment, the invention provides for a method of stabilizing an antigen-binding polypeptide or protein, comprising the step of mixing the antigen-binding polypeptide or protein with a liquid vehicle comprising a semifluorinated alkane of the formula RFRH, wherein RF is a linear perfluorinated hydrocarbon segment with 4 to 12 carbon atoms, and wherein RH is a linear alkyl group with 4 to 8 carbons, to form a suspension or dispersion.

DETAILED DESCRIPTION OF THE INVENTION

Figure 1:
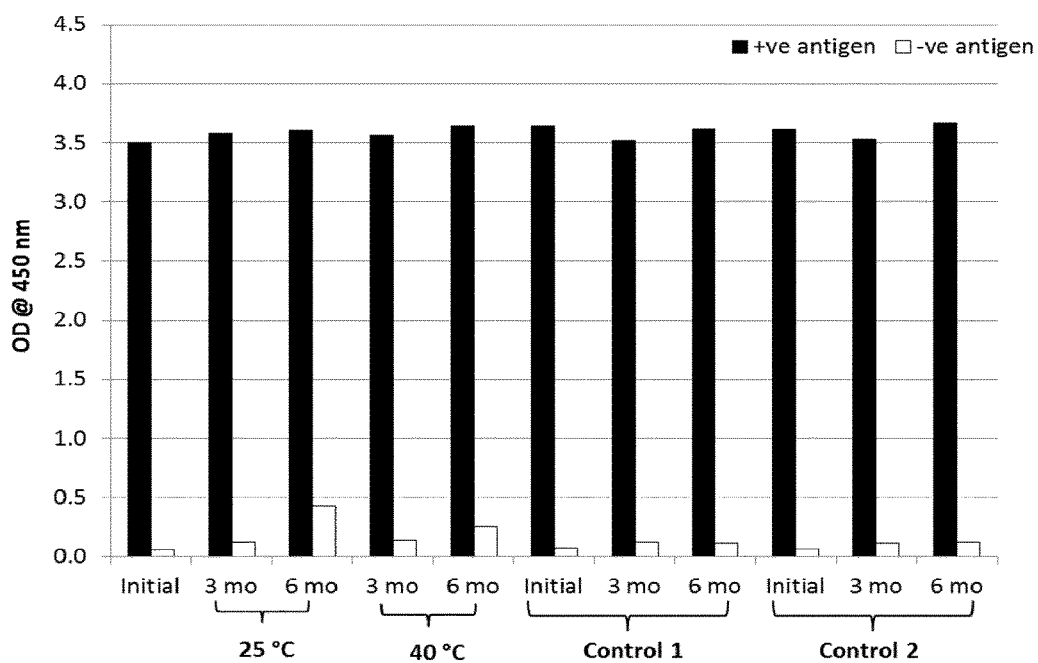
FIG. 1. Binding activities of anti-ECSCR antibody in F6H8 stored at 25° C. or 40° C. for 3 or 6 months compared to initial time point of reconstitution and to control samples of lyophilized antibody samples stored at −80° C. and never-lyophilized samples stored in PBS at 4° C. (Example 1).

In a first aspect, the present invention provides compositions comprising an antigen-binding polypeptide or protein and a liquid vehicle which comprises a semifluorinated alkane of the formula RFRH, wherein RF is a linear perfluorinated hydrocarbon segment with 4 to 12 carbon atoms, and wherein RH is a linear alkyl group with 4 to 8 carbons. Moreover, the antigen-binding polypeptide or protein is incorporated in the composition such as to form a dispersion or a suspension; i.e. the antigen-binding polypeptide or protein is dispersed or suspended in the liquid vehicle.

Semifluorinated alkanes provide a number of advantages from the pharmaceutical perspective. They are substantially non-toxic and are found to be well-tolerated by various types of human and animal tissue when administered topically or parenterally. In addition, they are chemically inert and are generally compatible with active and inactive ingredients in pharmaceutical formulations. They are also capable of dissolving a large range of compounds, such as small molecule active ingredients and many common pharmaceutically acceptable excipients, probably due to their inherent amphiphilicity. Moreover, semifluorinated alkanes, when acting as vehicles for compounds that are not soluble or poorly soluble (such as antigen-binding proteins or polypeptides), form dispersions or suspensions with very useful physical or pharmaceutical properties, i.e. with little or no tendency to form solid, non-dispersible sediments.

It has been found by the inventors that the presence of a semifluorinated alkane as a liquid vehicle in a composition comprising an antigen-binding protein or polypeptide has a remarkable stabilizing effect on these components. In particular, compositions comprising semifluorinated alkane as a liquid vehicle are capable of substantially preventing or inhibiting their aggregation and reducing chemical degradation over a substantial period of time, at room temperature and even at higher temperatures such as 40° C., without loss of biological activity.

It has also been found that antigen-binding protein dispersions and suspensions in semifluorinated alkanes exhibit a remarkable degree of physical stability. The occurrence of flotation or sedimentation takes place slowly, leaving sufficient time for the withdrawal of a dose after gentle shaking or swirling of the container (e.g. a vial) with the dispersion or suspension. The antigen-binding protein particles in semifluorinated alkane appear to largely retain their original particle size distribution, and are readily redispersible; poorly re-dispersible aggregates do not appear to be formed. Importantly, this provides for a higher level of dosing accuracy in terms of precision and reproducibility.

In contrast, suspensions or dispersions in other chemically inert vehicles tend to be unstable, leading to formation of dense and poorly redispersible aggregates, and making precise dosing challenging, or in some cases, impossible, such as leading to the clogging of fine-gauged needles typically used for subcutaneous injections. Aggregated protein particles also present a high risk towards triggering adverse immunogenic reactions.

Suspensions or dispersions that are unstable tend to separate quickly by flotation of the dispersed phase, or by its sedimentation, depending on the relative densities of the dispersed phase and of the continuous phase. Such behaviour is usually accompanied by rapid formation of dense and poorly re-dispersible aggregates. Rapid flotation or sedimentation makes accurate and reproducible dosing challenging, if not impossible. For example, if an injectable or ophthalmic suspension settles rapidly after shaking, and if a first dose from the full container is not withdrawn immediately after shaking, a dose that is withdrawn may contain a lower-than-intended number of drug particles (or if the container is held upside down, a large-than-intended dose will be dispensed). Later doses withdrawn from the same container will also then contain either too high or too low of a drug-dose per volume. Vigorous shaking of antigen-binding polypeptides and proteins in attempt to re-disperse poorly re-dispersible aggregates may also further trigger their further aggregation and deterioration.

Key advantages of the present invention are brought about by the presence of a semifluorinated alkane in the composition, functioning as a liquid vehicle. The advantageous properties of semifluorinated alkane-based suspensions result in superior pharmaceutical quality and performance characteristics, and also increase the convenience of use for the patient and/or the healthcare provider.

Semifluorinated alkanes are linear or branched alkanes some of whose hydrogen atoms have been replaced by fluorine. In the semifluorinated alkanes (SFAs) used in the present invention, one linear non-fluorinated hydrocarbon segment and one linear perfluorinated hydrocarbon segment are present. These compounds thus follow the general formula $F(CF_2)_n(CH_2)_mH$. According to the present invention, n is selected from the range of 4 to 12, and m is selected from the range of 4 to 8.

A nomenclature which is frequently used for semifluorinated alkanes designates a perfluorated hydrocarbon segment as RF and a non-fluorinated segment as RH. Alternatively, the compounds may be referred to as FnHm and FnHm, respectively, wherein F means a perfluorated hydrocarbon segment, H means a non-fluorinated segment, and n and m define the number of carbon atoms of the respective segment. For example, F3H3 is used for perfluoropropylpropane, $F(CF_2)_3(CH_2)_3H$. Moreover, this type of nomenclature is usually used for compounds having linear segments. Therefore, unless otherwise indicated, it should be assumed that F3H3 means 1-perfluoropropylpropane, rather than 2-perfluoropropylpropane, 1-perfluoroisopropylpropane or 2-perfluoroisopropylpropane.

Preferred semifluorinated alkanes include in particular the compounds F4H5, F4H6, F4H8, F6H4, F6H6, F6H8, and F6H10. Particularly preferred for carrying out the invention are F4H5, F4H6, F6H6 and F6H8. In another particularly preferred embodiment, the composition of the invention comprises F6H8.

Optionally, the composition may comprise more than one SFA. It may be useful to combine SFAs, for example, in order to achieve a particular target property such as a certain density or viscosity. If a mixture of SFAs is used, it is furthermore preferred that the mixture comprises at least one of F4H5, F4H6, F6H4, F6H6, F6H8, and F6H10, and in particular one of F4H5, F4H6, F6H6 and F6H8. In another embodiment, the mixture comprises at least two members selected from F4H5, F4H6, F6H4, F6H6, F6H8, and F6H10, and in particular at least two members selected from F4H5, F6H6 and F6H8.

Liquid SFAs are chemically and physiologically inert, colourless and stable. Their typical densities range from 1.1 to 1.7 $g/cm^3$, and their surface tension may be as low as 19 mN/m. SFAs of the RFRH type are insoluble in water but also somewhat amphiphilic, with increasing lipophilicity correlating with an increasing size of the non-fluorinated segment.

Liquid SFAs of the RFRH type are being used commercially for unfolding and reapplying a retina, for long-term tamponade as vitreous humour substitute (H. Meinert et al., European Journal of Ophthalmology, Vol. 10(3), pp. 189-197, 2000), and as wash-out solutions for residual silicon oil after vitreo-retinal surgery. Experimentally, they have also been used as blood substitutes (H. Meinert et al., Biomaterials, Artificial Cells, and Immobilization Biotechnology, Vol. 21(5), pp. 583-95, 1993). These applications have established SFAs as physiologically well tolerated compounds. On the other hand, SFAs have not been used as excipients in approved drug products as of today.

The composition of the invention comprises an antigen-binding polypeptide or protein. Polypeptides and proteins in general represent polymers of amino acid units that linked to each other by peptide bonds. Since the size boundaries that are often used to differentiate between polypeptides and proteins are somewhat arbitrary, the two expressions for these molecules should—within the context of the present invention—not be understood as mutually exclusive: A polypeptide may also be referred to as a protein, and vice versa. Typically, the term "polypeptide" only refers to a single polymer chain, whereas the expression "protein" may also refer to two or more polypeptide chains that are linked to each other by non-covalent bonds.

More specifically, and as used within the context of the present invention, antigen-binding polypeptides or proteins refer to full-length and whole antibodies (also known as immunoglobulins) in their monomer, or polymeric forms and any fragments, chains, domains or any modifications derived from a full-length antibody capable of specifically binding to an antigen. The antigen-binding polypeptides or proteins may belong to any of the IgG, IgA, IgD, IgE, or IgM immunoglobulin isotypes or classes. Fusion proteins comprising an antibody fragment capable of specifically binding to an antigen and antibody-drug conjugates are also within the definition of antigen-binding polypeptides or proteins as used herein.

A full-length antibody is a Y-shaped glycoprotein comprising of a general structure with an Fc (fragment crystallisable) domain and a Fab (fragment antigen binding) domain. These are structurally composed from two heavy (H) chains and two light (L) chain polypeptide structures interlinked via disulfide bonds to form the Y-shaped structure. Each type of chain comprises a variable region (V) and a constant region (C); the heavy chain comprises a variable chain region ($V_H$) and various constant regions (e.g. $C_H1$, $C_H2$, etc.) and the light chain comprises a variable chain region ($V_L$) and a constant region (CO. The V regions may be further characterized into further sub-domains/regions, i.e. framework (FR) regions comprising more conserved amino acid residues and the hypervariable (HV) or complementarity determining regions (CDR) which comprise of regions of increased variability in terms of amino acid residues. The variable regions of the chains determine the binding specificity of the antibody and form the antigen-binding Fab domains of an antibody.

In a preferred embodiment of the invention, the compositions comprise an antigen-binding polypeptide or protein, wherein the antigen-binding polypeptide or protein is selected from a monoclonal antibody, polyclonal antibody, an antibody fragment, a fusion protein comprising an antibody fragment, an antibody-drug conjugate, or any combination thereof.

In a particularly preferred embodiment of the invention, the compositions comprise an antigen-binding polypeptide or protein selected from a monoclonal antibody (mAb). A monoclonal antibody refers to an antibody obtained from a homogenous population of antibodies that are specific towards a single epitope or binding site on an antigen. Monoclonal antibodies may be produced using antibody engineering techniques known in the art, such as via hybridoma or recombinant DNA methods.

Also within the scope of antigen-binding polypeptides and proteins, and monoclonal antibodies are antibody fragments. As defined herein, antibody fragments include any region, chain, domain of an antibody, or any constructs or conjugates thereof that can interact and bind specifically to an antigen, and may be monovalent, bivalent, or even multivalent with respect to binding capability. Such antibody fragments may be produced from methods known in the art, for example, dissection (e.g. by proteolysis) of a full-length native antibody, from protein synthesis, genetic engineering/DNA recombinant processes, chemical cross-linking or any combinations thereof. Antibody fragments are commonly derived from the combination of various domains or regions featured in variable V region of a full-length antibody.

In an embodiment of the invention, the compositions comprise an antigen-binding polypeptide or protein selected from an antibody fragment, wherein the antibody fragment is a fragment antigen-binding (Fab), a single-chain variable fragment (scFv), a single-domain antibody, a minibody, or a diabody.

Particularly preferred antibody fragments are fragment antigen-binding domains (Fab, also referred to as Fab') or Fab dimers comprising of two Fab fragments linked by a disulfide linkage. Examples of Fabs are abciximab, certolizumab, digifab, and ranibizumab. A preferred Fab is certolizumab (also known as certolizumab pegol), which is a recombinant humanized antibody Fab' fragment conjugated to polyethylene glycol. Certolizumab has a molecular mass of 91 kDa and is directed against tumour necrosis factor alpha (TNFα).

In yet another embodiment of the invention, the compositions may comprise a single-chain variable fragment (scFv) such as those comprising of heavy ($V_H$) and light ($V_L$) chain variable domains joined by a linker or a complexed multimeric/multivalent constructs thereof, for example, diabodies (bivalent dimer), triabodies (trivalent trimer), or tetrabodies (tetravalent tetramer). Multimeric antibody fragments may also be multispecific, for example, a bispecific diabody may comprise of two fragments each with specificity for a different antigen. Further preferred antibody fragments include single domain antibodies (daBs) such as those comprising a single $V_H$ or $V_L$ domain capable of specifically binding to an antigen. Antibody fragments also within the scope of the invention include scFv-$C_H$ dimer constructs i.e. a minibody.

According to a further embodiment, the composition comprises an antigen-binding polypeptide or protein with a molecular mass selected from at least 10 KDa, at least 15 kDa, at least 35 kDa, at least 50 kDa, at least 70 kDa, or at least 90 kDa. Also preferred is an antigen-binding polypeptide or protein with a molecular mass of at least 100 kDa, such as 100-150 kDa, or even higher than 150 kDa. Particularly preferred are antigen-binding polypeptides or proteins with a molecular mass in the range of 70 kDa to 160 kDa.

In a further embodiment of the invention, the antigen-binding polypeptide or protein may be selected from a fusion protein comprising an antibody fragment. An antibody fragment may be fused to another bioactive protein or polypeptide fragment, for example, a polypeptide toxin, enzyme, cytokine, membrane protein, etc. Examples of a fusion protein comprising an antibody fragment include etanercept and atacicept. Etanercept is a recombinant human protein with a molecular mass of 150 kDa, comprising the ligand binding portion of 75 kDa tumor necrosis factor receptor (TNFR) fused to the Fc portion of IgG1.

In another embodiment of the invention, the antigen-binding polypeptide or protein may be selected from an antibody-drug conjugate, wherein the antigen-binding polypeptide or protein is covalently linked, for example via a linker or chemically cross-linking to a small molecule drug or a radiolabelled component such as radionuclides. Examples of antibody-drug conjugates include gemtuzumab ozogamicin, brentuximab vedotin, $^{90}$Y-labelled ibritumomab tiuxetan, $^{131}$I-labelled tositumomab, $^{99}$mTc-labelled arcitumomab. As used herein, the term antibody-drug conjugate may also refer to an antigen-binding polypeptide or protein that is substantially chemically modified, for example, by PEGylation (e.g. certolizumab pegol, a PEGylated Fab' fragment of a humanized TNF inhibitor monoclonal antibody) or lipidation.

As understood herein, antigen-binding polypeptides and proteins may be chimeric, humanized or human. Chimeric monoclonal antibodies, for example, refer to hybrid monoclonal antibodies comprising domains or regions of the heavy or light chains derived from antibody sequences from more than one species, for example from murine and human antibody sequences. Humanized monoclonal antibodies refer to those that are predominantly structurally derived from human antibody sequences, generally with a contribution of at least 85-95% human-derived sequences, whereas the term human refer to those are derived solely from human germline antibody sequences. In a preferred embodiment, the compositions comprise of an antigen-binding polypeptide or protein selected from a monoclonal antibody, wherein the monoclonal antibody is a chimeric, humanized, or human antibody.

In another embodiment, the composition may comprise a polyclonal antibody, or a heterogenous mixture of antibodies capable of recognizing more than one epitope of an antigen.

In a preferred embodiment, the antigen-binding polypeptide or protein is a therapeutic or diagnostic compound or a vaccine. As used herein, a therapeutic compound is a compound that is useful for preventing a disease or condition, alleviating any symptoms of a disease or condition, improving any disease or condition, delaying the progress of a disease or condition or the like. A diagnostic compound is useful for determining the state of an organism, or for diagnosing a disease, condition, symptom, or patient phenotype. The therapeutic compound must be administered to the patient, whereas the diagnostic agent may be used in vivo or in vitro, depending on the specific case. For the avoidance of doubt, the therapeutic or diagnostic compound is incorporated within the composition of the invention in a therapeutically or diagnostically effective amount.

In a particularly preferred embodiment, the compositions of the invention comprise a monoclonal antibody or antibody fragment that is therapeutically effective or which may be administered for the treatment of a disease or condition, such as an autoimmune disease or inflammatory condition, a neurological disorder, or cancer. Exemplary monoclonal antibodies or antibody fragments for the treatment of cancer include alemtuzumab, bevacizumab, cetuximab, gemtuzumab, ipilimumab, ibritumomab, nimotuzumab, ofatumumab, panitumumab, rituximab, tositumomab, and trastuzumab. Exemplary monoclonal antibodies or antibody fragments for the treatment of autoimmune or inflammatory conditions include adalimumab, alemtuzumab, belimumab, briakinumab, canakinumab, eculizumab, epratuzumab, efalizumab, golimumab, infliximab, mepolizumab, natalizumab, ofatumumab, ocrelizumab, otelixizumab, omalizumab, reslizumab, rituximab, teplizumab, tocilizumab, ustekinumab, and vedolizumab. Further examples of monoclonal antibodies or antibody fragments which may be administered for the treatment, prevention or diagnosis of a disease or condition include basiliximab, daclizumab, denosumab, eculizumab, palivizumab, and motavizumab.

Suspension or dispersion compositions according to the invention may in particular comprise a cancer therapy agent selected from an antigenbinding polypeptide or protein such as a monoclonal antibody, polyclonal antibody, an antibody fragment, a fusion protein comprising an antibody fragment, an antibody-drug conjugate, or any combination thereof and a liquid vehicle comprising a semifluorinated alkane of the formula RFRH wherein RF is a linear perfluorinated hydrocarbon segment with 4 to 12 carbon atoms, and wherein RH is a linear alkyl group with 4 to 8 carbon atoms. Antigen binding polypeptides or proteins which act as angiogenesis inhibitors or which are able to inhibit tumour cell proliferation (anti-proliferative agent) are particularly relevant. The antibody fragment may be a fragment antigen-binding (Fab), a single-chain variable fragment (scFv), a single-domain antibody, a minibody, or a diabody.

For example, a composition according to the invention may comprise of bevacizumab and a liquid vehicle, wherein the liquid vehicle comprises a semifluorinated alkane of the formula RFRH, wherein RF is a linear perfluorinated hydrocarbon segment with 4 to 12 carbon atoms, and wherein RH is a linear alkyl group with 4 to 8 carbon atoms; and wherein bevacizumab is incorporated in the composition in the form a dispersion or suspension. Antigen-binding fragments of bevacizumab are also contemplated. Bevacizumab (tradename Avastin®) is a humanized murine antibody that targets VEGF-A (vascular endothelial growth factor A) and which acts as an angiogenesis inhibitor. Compositions of the invention comprising bevacizumab may be used for the treatment or prevention of diseases and conditions such as colorectal, lung, breast, renal or brain (glioblastoma) cancers, as well as eye conditions such as age-related macular degeneration (AMD).

Further compositions may comprise the antibodies known under the pipeline name as Fsn0503 and Fsn1006. Fsn1006 is a dual-specific antibody that can bind to the human EGFR (epidermal growth factor receptor) ligands amphiregulin and HB-EGF (heparin-binding epidermal growth factor), and which can act to inhibit cell-proliferation. Fsn1006 is a humanized IgG1/kappa isotype. It has been demonstrated that Fsn1006 works independently of the K-ras mutational status of the cell and therefore has significant advantages over current EGFR targeting properties such as cetuximab. Fsn0503 is also a humanized IgG1/kappa antibody that targets and inhibits the proteolytic activity of human Cathepsin S. Fsn0503 may be used in the treatment of cancer, and other angiogenesis related diseases, in particular diseases where Cathepsin S-mediated remodelling of the extracellular matrix is involved.

In a yet a further preferred embodiment, suspension or dispersion compositions according to the invention may comprise a TNF inhibitor selected from an antigen-binding polypeptide or protein such as an monoclonal antibody, polyclonal antibody, an antibody fragment, a fusion protein comprising an antibody fragment, an antibody-drug conjugate, or any combination thereof, and a liquid vehicle comprising a semifluorinated alkane of the formula RFRH wherein RF is a linear perfluorinated hydrocarbon segment with 4 to 12 carbon atoms, and wherein RH is a linear alkyl group with 4 to 8 carbon atoms. Exemplary TNF inhibitors are infliximab, etanercept and certolizumab and their biosimilars. Compositions of the invention may comprise these TNF inhibitors and a liquid vehicle, wherein the liquid vehicle consists of semifluorinated alkane selected from F4H5, F4H6, F4H8, F6H4, F6H6, F6H8, and F6H10. In particular, these compositions may be used in the therapy of autoimmune diseases affecting the gastrointestinal system such as Crohn's disease, ulcerative colitis, or conditions affecting the joints and skin such as rheumatoid arthritis, psoriatic arthritis, ankylosing spondylitis and plaque psoriasis.

In yet another embodiment, the compositions of the invention comprise an antigen-binding polypeptide or protein at a concentration of preferably at least 0.5 mg/mL, such as 0.5-10 mg/ml. In further preferred embodiments, the concentration is at least 1 mg/mL, at least 5 mg/mL, at least 10 mg/mL, at least 15 mg/mL, at least 25 mg/mL or at least 35 mg/mL.

In a further aspect, the current invention presents a method of stabilizing an antigen-binding polypeptide or protein, comprising the step of mixing the antigen-binding polypeptide or protein with a liquid vehicle comprising a semifluorinated alkane. The semifluorinated alkane is of the formula RFRH, wherein RF is a linear perfluorinated hydrocarbon segment with 4 to 12 carbon atoms, and wherein RH is a linear alkyl group with 4 to 8 carbon atoms. According to the method, the step of mixing the antigen-binding polypeptide or protein with the liquid vehicle is performed such as to form a suspension or a dispersion. Such method of stabilizing an antigen-binding polypeptide or protein may be useful for the preparation of a composition for use as a medicine, such as in the treatment, prevention or diagnosis of a disease or condition in a patient in need thereof. Optionally, such method of stabilization may also be used for the preparation, manufacture or synthesis of an antigen-binding polypeptide or protein.

As used herein, the term stability is defined as the maintenance of the chemical or physical integrity and/or bioactivity of the antigen-binding polypeptide or protein over a period of time. Stabilizing an antigen-binding polypeptide or protein includes the prevention or delay of degradation or deterioration of the antigen-binding polypeptide or protein from its biologically and/or therapeutically active form to an inactive form. Instability may arise from events such as aggregation, denaturation, fragmentation, or chemical modifications such as oxidation, cross-linking, deamidation and reactions with other components featured in the composition comprising the antigen-binding polypeptide or protein.

The stability of the antigen-binding protein or polypeptide in the composition may be characterized using known methods in the art, including but not limited to, measurement of biological activity such as antigen-binding activity with immunoassay techniques such as ELISA, or other techniques of determining purity or physical/chemical changes to the antigen-binding protein or polypeptide such as size exclusion chromatography, capillary gel electrophoresis, circular dichroism, or mass spectrometry. Stability is determined by comparison of measurements obtained via these types of characterization methods at an initial time point, such as at the time of formulation or preparation of the composition (i.e., as the case may be, the suspension or dispersion), and those obtained at a later time point, that is, after storage in a given environment or condition.

It has been found by the inventors that an antigen-binding protein in a liquid vehicle comprising a semifluorinated alkane remains stable at 25° C. for at least 6 months. More remarkably, the antigen-binding protein was comparably stable when stored at a temperature of 40° C. over the same period of time. That is, the composition comprising the antigen-binding protein retained effectively the same or similar antigen-binding activity to its initial antigen-binding activity.

In a preferred embodiment, the compositions of the invention retain at least 85% or at least 90%, such as 90-95%, or even more than 95% of their initial antigen-binding activity during storage of 3 months at 25° C., or at room temperature, or at a temperature between room temperature and 40° C. In another preferred embodiment, the compositions of the invention retain at least 85% or at least 90%, such as 90-95%, or even more than 95% of their initial antigen-binding activity, during storage of 6 months at 25° C., or at room temperature (RT), or at a temperature between RT and 40° C. In yet another embodiment, the compositions of the invention retain at least 85% of their initial antigen-binding activity, during storage of 6 months between RT and 40° C. and a relative humidity of between 50-75%. In other embodiments, the time period of storage may be 4-6 weeks, 6-12 weeks, or 3-6 months or 6-12 months. In further embodiments, the humidity (RH) during storage may be at least 40% or at least 50%, or at least 65% or at least 75%.

As mentioned, the antigen-binding polypeptide or protein is incorporated in the composition such as to form a dispersion or suspension. In other words, the antigen-binding polypeptide or protein is dispersed or suspended in the liquid vehicle comprising a semifluorinated alkane. Whether a suspension is formed upon dispersing the antigen-binding protein in the liquid carrier depends e.g. on the nature of the antigen-binding protein, its concentration in the carrier, and the selected SFA(s).

As used herein, a suspension may be defined as a type of dispersion, i.e. a system having at least one continuous (or coherent) phase and at least one discontinuous (or inner) phase which is dispersed in the continuous phase. In a suspension, the dispersed phase is in the solid state. The suspensions useful for practising the invention are liquids, at least at physiological temperature, which means that the continuous phase is a liquid. Typically, the suspensions are also liquid at room temperature. Beyond suspensions, the term dispersions is understood to include colloidal systems in which an antigen-binding protein and polypeptide is finely dispersed in the liquid phase. In some embodiments, the antigen-binding polypeptide or protein is also at least partially solvated.

A stabilized suspension or dispersion of an antigen-binding polypeptide or protein is prepared via a method comprising the step of mixing the antigen-binding polypeptide or protein with a liquid vehicle comprising a semifluorinated alkane. The stability of the resulting suspension or dispersion may be characterized by the measurement of various physical attributes including but not limited to, for example the re-dispersibility of the suspended particles, particle size distribution and particle size growth over time, using such methods as those known in the art.

In one particular embodiment, the composition comprises only the antigen-binding polypeptide or protein and one or more SFAs, i.e. the composition consists of the antigen-binding polypeptide or protein and one or more SFAs as defined above. In another preferred embodiment, the composition comprising an antigen-binding polypeptide or protein and one or more SFAs is effectively or substantially free of water, i.e. the composition comprises no water, except perhaps for residual amounts of water introduced via other solid or liquid components or the antigen-binding polypeptide or protein itself. In other cases, the suspension or dispersion compositions comprising an antigen-binding polypeptide or protein and a liquid vehicle comprising a semifluorinated alkane may be water-free.

In contrast to some other suspensions or dispersions known in prior art, the formulations of the invention require no surfactant, or only small amounts of surfactant, for their physical stabilisation. This is a significant advantage as surfactants have a substantial potential for irritation and local toxicity, especially when administered by subcutaneous or intramuscular injection or by instillation into the eye. According to one of the preferred embodiments, the compositions of the invention are substantially free of surfactant. In a further embodiment, the total amount of surfactant or surfactants, if more than one surfactant is incorporated, is not more than about 10 wt.-%, in particular not more than about 5 wt.-%, or preferably not more than about 2 wt.-%, respectively. In further preferred embodiments, the amount is not more than about 1 wt.-%, or not more than about 0.5 wt.-%, respectively. In this context, the SFAs as described herein, although they possess some amphiphilic properties due to their chemical structure which includes fluorinated and non-fluorinated alkyl (or alkylene) groups characterised by different degrees of lipophilicity, are not understood as being within the scope of surfactants.

The surfactants which are absent or only present in small amounts include non-ionic, cationic, anionic, and zwitterionic surfactants as commonly used as excipients in various types of pharmaceutical compositions, e.g. as wetting agents, emulsifiers, dispersing agents, solubilisers and the like. Examples of surfactants which are considered potentially useful include tyloxapol, poloxamers such as Pluronic F68LF or Lutrol F68, Pluronic L-G2LF and Pluronic L62D, polysorbates such as polysorbate 20 and polysorbate 80, polyoxyethylene castor oil derivatives, sorbitan esters, polyoxyl stearates, lecithins, purified or synthetic phospholipids, and mixtures of two or more thereof.

The compositions of the invention may optionally comprise a non-fluorinated organic liquid, for example in order to modify the properties of the liquid vehicle, such as the viscosity. Such other liquid may be an oil selected from glyceride oils, liquid waxes, and liquid paraffin, or an organic solvent exhibiting a high degree of biocompatibility, or a mixture of more than one liquid excipients.

Examples of potentially useful oily excipients which may be used in combination with one or more SFA's include triglyceride oils (i.e. soybean oil, olive oil, sesame oil, cotton seed oil, castor oil, sweet almond oil), mineral oil (i.e. petrolatum and liquid paraffin), medium chain triglycerides (MCT), oily fatty acids, isopropyl myristate, oily fatty alcohols, esters of sorbitol and fatty acids, oily sucrose esters, or any other oily substance which is physiologically tolerated by the eye.

Examples of potentially useful organic solvents include glycerol, propylene glycol, polyethylene glycol, and ethanol. The concentration of the cosolvent should preferably be low relative to that of the SFA or SFA mixture. If an organic solvent such as ethanol is used, it is recommendable to keep it below a level of approx. 5 wt.-%. More preferably, the content of ethanol is from about 0.1 to about 2 wt.-%, and most preferably not more than about 1 wt.-%.

The composition may of course comprise further pharmaceutical excipients as required or useful. Potentially useful excipients include acids, bases, antioxidants, stabilisers, synergists, colouring agents, thickening agents, and—if required in a particular case—a preservative. Generally, however, the invention provides a means of formulating non-aqueous compositions which are microbiologically stable. This is due to the fact that SFAs are not normally prone to microbial contamination. Hence, it is possible to formulate preservative-free compositions to be filled in multi-use containers. Preservative-free compositions are better tolerated by many patients and enable lower costs of final goods.

The liquid suspensions of the invention may be prepared by conventional methods. In principle, the solid particles comprising the active ingredient may be dispersed in the liquid vehicle comprising the SFA. Alternatively, the particles may be precipitated in situ by adding a—typically organic—solution of the active ingredient (and, optionally, one or more solid excipients) under controlled conditions to the SFA-based vehicle.

The solid particles may be prepared by lyophilization or spray-drying of a solution of the antigen-binding proteins or particles. The solution may be aqueous or non-aqueous and may further comprise pharmaceutical excipients as may be useful or required.

The particle size of the dispersed phase may be also adjusted before or after the particles are combined with the liquid vehicle. In one of the preferred embodiments, particles of the active ingredient are provided which already have the appropriately selected particle size. Powders having such selected particle size may be obtained directly from the synthesis of the respective compound by crystal engineering, or after synthesis by conventional grinding or milling methods using standard equipment such as a ball mill, hammer mill, roller mill, colloidal mill, jet mill, or the like. If the particle size is to be reduced after preparation of a suspension, ultrasonication as well as various types of homogenisers may be used, such as colloid mills or high pressure homogenisers.

The current invention also provides for a method for treating, preventing or diagnosing a disease or condition in a patient in need thereof, comprising the step of administering to the patient a composition, preferably in the form of a suspension or dispersion, comprising an antigen-binding polypeptide or protein and a liquid vehicle, wherein the liquid vehicle comprises a semifluorinated alkane. The superior physical properties of the suspensions according to the invention render these compositions particularly useful for topical administration to the eye of a patient, to the ear, nose or lung, or parenterally by injection. For example, the compositions of the invention may be administered to the eye of a patient by topical application or injection. Preferred modes of injection include dermal, subcutaneous, intramuscular, and locoregional injection. Most preferred are the subcutaneous and intramuscular routes of administration.

EXAMPLES

Example 1

The stability of an anti-ECSCR (endothelial cell-specific chemotaxis regulator) monoclonal antibody (clone id 13G11 1A31 A7, a murine IgG/k antibody expressed from hybridoma cells that binds to the endothelial marker ECSCR) in F6H8 at 25° C. and at 40° C. was studied over a period of 6 months.

Lyophilized 0.25 mg samples of the anti-ECSCR monoclonal antibody (originally stored at −80° C. in PBS buffer) were reconstituted to a concentration of 1 mg/mL in F6H8. The reconstituted samples were stored in crimped glass vials at 25° C./60% RH and at 40° C./75% RH. The binding activities of these samples were determined after 3 months and 6 months of storage.

To serve as a first control, other samples of the lyophilized antibody were stored in the lyophilized form at −80° C. These were reconstituted in PBS only prior to analysis. A second control consisted of samples of the antibody in PBS which were never lyophilized, but kept under refrigeration at 4° C.

The binding activities of the antibody samples to ECSCR antigen were determined by ELISA using the following protocol:

A Nunc MaxiSorp™ flat bottom Elisa plate was prepared by coating with ECSCR antigen and an unrelated negative antigen. The antigens were diluted in a coating buffer at a concentration of 1 µg/mL and incubated with the plates overnight at 4° C. The plates were then blocked with 200 µL of 3% blocking solution and incubated at RT on a shaker for 1-2 hours, followed by three washes with PBS-Tween 20 solution and blotted dry. The antibody samples were diluted to 1 µg/mL in PBS. 100 µg or 10 ng of each diluted sample was added to a well coated with the ECSCR antigen and a well coated with the negative control antigen. The plate was incubated at RT for 1 h on a shaker, then washed with PBS-Tween 20 and blotted dry. The antibody aliquots were probed with goat-anti-mouse IgG-HRP secondary antibody conjugate (Biorad, Catalogue Nr. 170-6516) at a 1:5000 dilution in PBS. The plates were incubated for 1 h at RT on a shaker, followed by three washes with PBS-Tween 20 solution and blotted dry. The plate was incubated at 37° C. for 10 min with 100 µL of TMB (3, 3', 5, 5'-tetramethylbenzidine), followed by addition of 50 µL/well of 1M HCl. Absorbance was measured at 450 nm with a spectrophotometer.

Comparison to the binding activities determined at the initial time point of reconstitution and the control samples show that the binding activity (determined from average of three samples) of the antibody in F6H8 stored at 25° C. or even at the higher temperature of 40° C. is maintained after storage over a 6-month period (FIG. 1). The binding activity is comparable to that observed for lyophilized anti-ECSCR monoclonal antibody samples stored at −80° C. (Control 1, FIG. 1) and for a never-lyophilized sample stored at 4° C. in PBS (Control 2, FIG. 1.)

Example 2

The stability of bevacizumab, Fsn1006 and Fsn0503 was studied at 25° C., 50° C., and 70° C. over a period of 4 weeks.

Lyophilization Protocol: Stock solutions of each of the antibodies listed above were obtained; Fsn1006 and Fsn0503 as solutions in PBS, bevacizumab (tradename Avastin®) in its commercial storage buffer. An equivalent of 80 mg of bevacizumab was transferred to >7000 MWCO dialysis tubing and dialysed for 72 hours against 3×2 L volumes of PBS. The antibody solutions were diluted to 0.5 mg/ml in PBS and 500 µl of each solution was aliquoted into individual 5-ml amber glass pharmaceutical grade vials for lyophilisation. Lyophilisation was done over a 48 hour cycle.

Resuspension of the lyophilized antibodies: The lyophilized antibodies were suspended in F4H5, F6H8, 50% vol F4H5 in F6H8, PBS (137 mM NaCl, 2.7 mM KCl, 10 mM $Na_2HPO_4$, 1.8 mM $KH_2PO_4$, pH=7.4) at a concentration of 0.5 mg/mL with careful vortexing. Resuspension of the lyophilized antibodies in PBS forms solutions, while suspensions were formed with the semifluorinated alkanes. The resulting suspensions and solutions were stored in amber glass vials at 25° C. and 50° C. for 4 weeks (28 days) After day 23, the 50° C. samples were subjected to 70° C. conditions.

The binding activities of the antibody samples were determined by ELISA testing at t=0 (immediately after resuspension), t=2 weeks and t=4 weeks. As a control, lyophilized antibodies samples which were never re-suspended (stored at −80° C.) and solutions of the antibodies in PBS which were never lyophilized (stored at 4° C.) were used.

ELISA Protocol: For the ELISA testing of each antibody, a Nunc Maxisorp 96 well plate was coated with the target antigen by adding 100 µg/well of the appropriate antigen in 100 µl 0.2 M carbonate buffer, pH 9.5 and incubated for 1 hour at 37° C. After washing with PBS containing 0.1% tween 20 (PBS-T), the plate was blocked by adding 200 µl 4% milk powder in PBS and incubating at room temperature for 2 hours on a shaker. After further washing, the antibody samples were applied. 1 ml of ×0.5 PBS was added to each non-aqueous vial. The antibody was extracted into the solution by gentle rocking for 5 minutes. 1 µl of the aqueous layer was then transferred to a vial containing 999 µl PBS (to give a nominal value of 50 µg/well). 100 µl of each sample vial was then plated in 6 replicates of 100 µl. The plates were incubated overnight at 4° C. After washing, the secondary antibody was applied (goat anti-human HRP conjugate) at a 1:60,000 dilution in PBS; 100 µl was added to each well and the plate was incubated for 1 hour at room temperature with shaking. The plates were then washed with 3 volumes of PBS-T followed by 2 volumes of PBS. 100 µl of TMB solution was then applied and the plate incubated for 10 minutes at 37° C. The reaction was stopped by the addition of 50 µl 1M HCl. Absorbance at λ=450 nm was read for each well.

TABLE 1

Bevacizumab Activity (Mean OD ± 2 SD at 450 nm)

| Week | F4H5 | F6H8 | 50% vol. F4H5 in F6H8 | PBS |
|---|---|---|---|---|
| 25° C. | | | | |
| 0 | 3.15 ± 0.19 | 3.26 ± 0.11 | 3.12 ± 0.12 | 3.04 ± 0.03 |
| 2 | 3.23 ± 0.05 | 2.34 ± 0.09 | 3.05 ± 0.10 | 2.12 ± 0.07 |
| 4 | 2.16 ± 0.36 | 2.23 ± 0.46 | 2.03 ± 0.56 | 0.30 ± 0.54 |
| 50° C. (70° C. last 5 days) | | | | |
| 0 | 3.16 ± 0.01 | 3.26 ± 0.11 | 3.14 ± 0.05 | 3.00 ± 0.05 |
| 2 | 3.27 ± 0.09 | 3.19 ± 0.10 | 3.06 ± 0.19 | 3.16 ± 0.08 |
| 4 | 1.63 ± 0.62 | 1.69 ± 0.34 | 1.64 ± 0.54 | 0.05 ± 0.003 |

TABLE 2

Fsn1006 Activity (Mean OD ± 2 SD at 450 nm)

| Week | F4H5 | F6H8 | 50% vol. F4H5 in F6H8 | PBS |
|---|---|---|---|---|
| 25° C. | | | | |
| 0 | 2.57 ± 0.20 | 2.47 ± 0.94 | 2.12 ± 0.21 | 2.63 ± 0.21 |
| 2 | 3.27 ± 0.13 | 3.32 ± 0.15 | 3.26 ± 0.10 | 2.99 ± 0.10 |
| 4 | 2.54 ± 0.30 | 2.43 ± 0.45 | 2.45 ± 0.38 | 0.62 ± 1.26 |
| 50° C. (70° C. last 5 days) | | | | |
| 0 | 2.56 ± 0.27 | 2.47 ± 0.94 | 2.26 ± 0.20 | 2.56 ± 0.24 |
| 2 | 3.32 ± 0.04 | 3.28 ± 0.04 | 2.81 ± 0.04 | 2.79 ± 0.13 |
| 4 | 2.01 ± 0.40 | 1.97 ± 0.24 | 1.80 ± 0.91 | 0.05 ± 0.01 |

TABLE 3

Fsn0503 Activity (Mean OD ± 2 SD at 450 nm)

| Week | F4H5 | F6H8 | 50% vol. F4H5 in F6H8 | PBS |
|---|---|---|---|---|
| 25° C. | | | | |
| 0 | 3.07 ± 0.10 | 3.06 ± 0.08 | 2.98 ± 0.22 | 3.11 ± 0.16 |
| 2 | 3.22 ± 0.23 | 3.22 ± 0.09 | 3.20 ± 0.08 | 2.01 ± 1.23 |
| 4 | 2.70 ± 0.19 | 2.43 ± 0.19 | 2.87 ± 0.24 | 0.72 ± 1.98 |
| 50° C. (70° C. last 5 days) | | | | |
| 0 | 3.09 ± 0.08 | 3.06 ± 0.08 | 3.07 ± 0.08 | 3.11 ± 0.07 |
| 2 | 3.26 ± 0.10 | 3.22 ± 0.12 | 3.18 ± 0.14 | 3.10 ± 0.21 |
| 4 | 2.64 ± 0.22 | 2.19 ± 0.18 | 2.73 ± 0.19 | 0.65 ± 1.91 |

The activity of bevacizumab, Fsn1006 and Fsn0503 stored as suspensions in F4H5, F6H8 and 50% vol F4H5 in F6H8 was substantially consistent during a 4-week period at both 25° C. and at 50° C., including the increase to a storage temperature of 70° C. for the 50° C. sample during the last five days of the period. In contrast the binding activity demonstrated by the solutions of these antibodies in PBS buffer deteriorated significantly by the end of the four-week period regardless of storage temperature.

Example 3

The binding activity of bevacizumab, Fsn1006, and Fsn0503 stored in SFA and PBS buffer at temperatures between 50° C. and 80° C. was examined.

The lyophilized antibodies bevacizumab, Fsn1006, and Fsn0503 (as prepared above in Example 2) were re-suspended in F4H5, F6H8, and PBS at a concentration of 0.5 mg/ml with careful vortexing. Re-suspension of these lyophilized antibodies in PBS yields solutions, while suspensions were formed with the SFAs.

The suspension/solution samples were held at temperatures of 50° C., 55° C., 60° C., 65° C., 70° C., 75° C., and 80° C. respectively for a period of 2 h and then cooled to 10° C. prior to PBS buffer extraction and activity assay using the ELISA method as described above in Example 2. Each experiment was performed in triplicate. Samples heated at 40° C. were used as a control.

Figure 2:
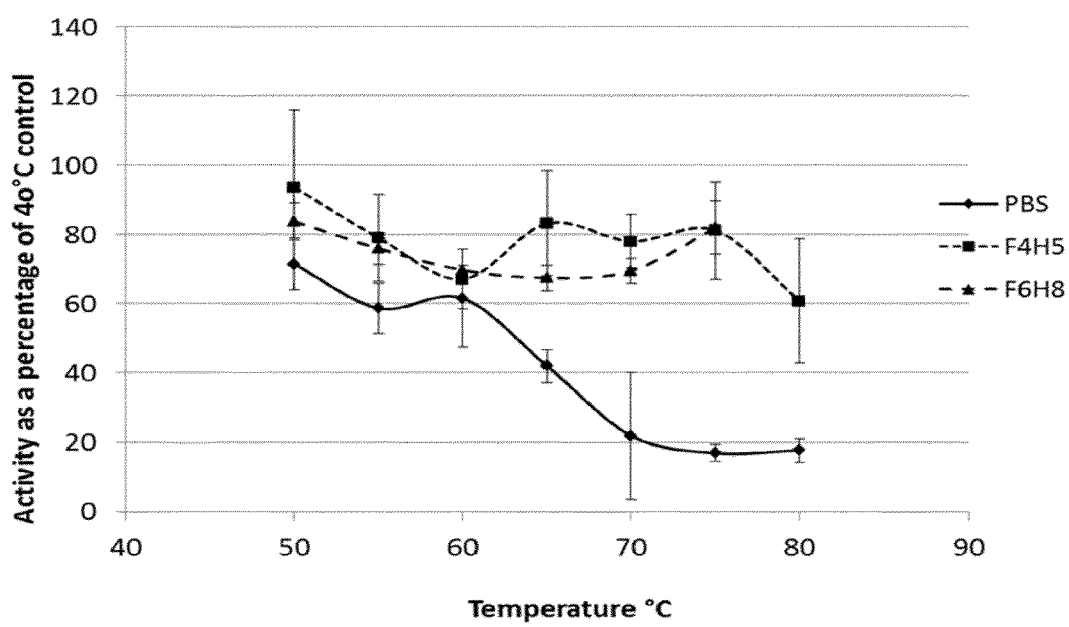
FIG. 2. Binding activity of bevacizumab antibody stored in F4H5 or F6H8 between 50° C. and 80° C., compared to the antibody stored in aqueous PBS buffer (Example 3).
Figure 3:
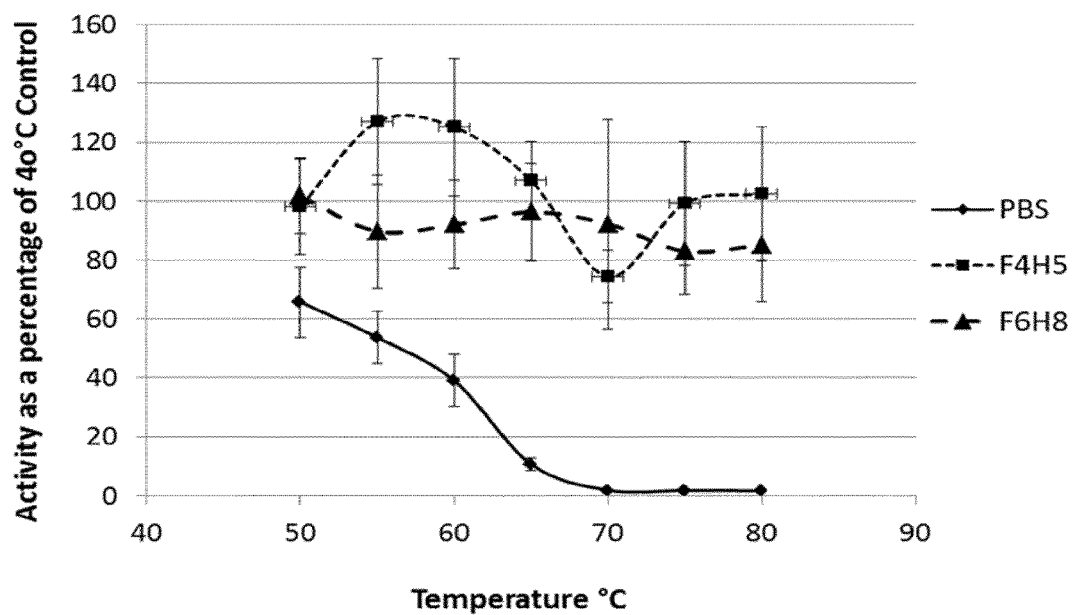
FIG. 3. Binding activity of Fsn1006 antibody stored in F4H5 or F6H8 between 50° C. and 80° C., compared to the antibody stored in aqueous PBS buffer (Example 3).
Figure 4:
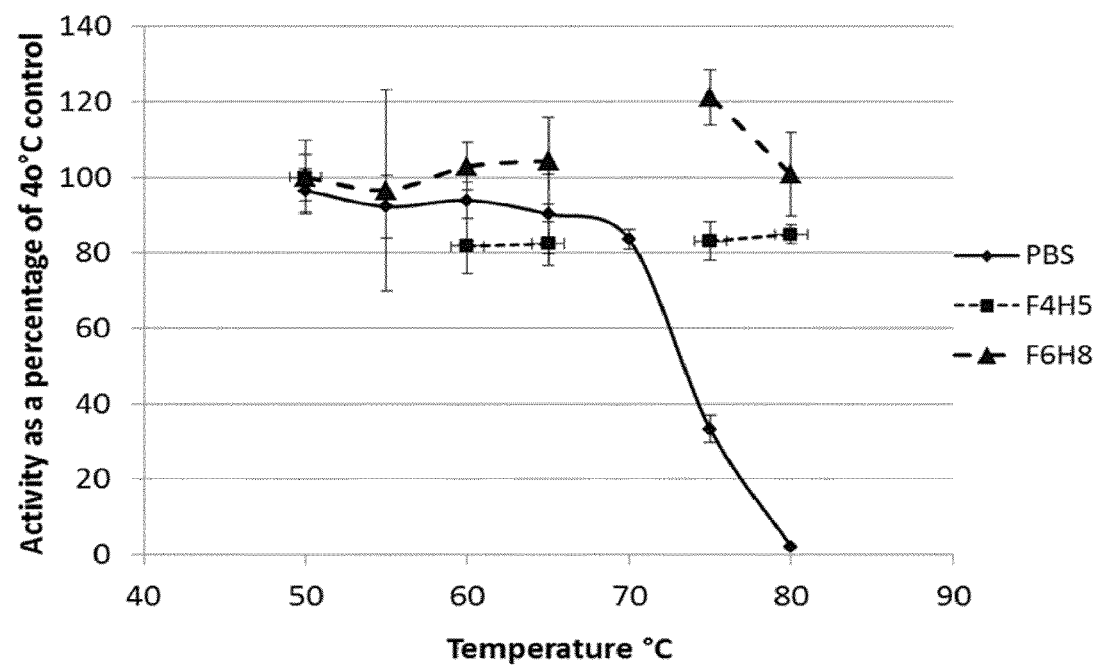
FIG. 4. Binding activity of Fsn0503 antibody stored in F4H5 or F6H8 between 50° C. and 80° C., compared to the antibody stored in aqueous PBS buffer (Example 3).

It was found that the bevacizumab (FIG. 2), Fsn1006 (FIG. 3) and Fsn0503 (FIG. 4) suspensions in F4H5 and F6H8 demonstrated significant stability towards thermal denaturation compared to the samples in aqueous buffer. Binding activity remained fairly constant between 50° C. and 80° C. for the antibodies formulated in these semifluorinated alkanes. In contrast, the activity of these antibodies stored in aqueous PBS buffer deteriorated sharply at temperatures above 60° C.

Example 4

The stability of a composition comprising an antigen-binding polypeptide or protein selected from infliximab (a chimeric monoclonal antibody with human constant and murine variable regions, and a molecular mass of 149 kDa), the fusion protein etanercept (a recombinant human protein with a molecular mass of 150 kDa comprising the ligand binding portion of the 75 kDa TNFR (tumor necrosis factor receptor) fused to Fc portion of IgG1), and certolizumab (an antibody fragment with a molecular mass of 91 kDa, comprising a recombinant Fab' conjugated to an approximately 40 kDa polyethylene glycol) or biosimilars thereof and a liquid vehicle comprising a semifluorinated alkane of formula RFRH wherein RF is a linear perfluorinated hydrocarbon segment with 4 to 12 carbon atoms, and wherein RH is a linear alkyl group with 4 to 8 carbon (for example F4H5 and F6H8) is studied and compared to formulations in different media.

The antibody is lyophilized and re-suspended in a semifluorinated alkane.

Comparative suspensions/solutions are also prepared in other media. The following stability tests are performed on these formulations:

Storage stability under ICH conditions (25 and 40° C.).
Temperature stability outside of ICH conditions, i.e. thermal denaturing These are carried out in analogy to the methods described in examples 1-3. Analytical methods suitable for assaying the stability of these antigen-binding polypeptides are performed. Assays to monitor the activity and potency of the antibody, as well as to monitor aggregation levels throughout the course of the stability experiments listed above include techniques such as ELISA in similarity to the protocol as described above in Examples 1-3.

The analytical methods are carried out with samples obtained directly from the antibody suspensions or depending on the analytical technique, on samples which are aqueous buffer extractions.

It is expected that the compositions comprising the antigen binding polypeptide or proteins will exhibit improved stability and a decreased propensity towards aggregate formation.

The invention claimed is:

1. A composition comprising an antigen-binding polypeptide or protein and a liquid vehicle, wherein the liquid vehicle comprises a semifluorinated alkane selected from F4H5, F4H6, F4H8, F6H4, F6H6, F6H8, and F6H10; and wherein the antigen-binding polypeptide or protein is incorporated in the composition such as to form a suspension; wherein the composition is substantially free of water.

2. The composition of claim 1, wherein the antigen-binding polypeptide or protein is selected from a monoclonal antibody, polyclonal antibody, an antibody fragment, a fusion protein comprising an antibody fragment, an antibody-drug conjugate, or any combination thereof.

3. The composition of claim 2, wherein the antibody fragment is a fragment antigen-binding (Fab), a single-chain variable fragment (scFv), a single-domain antibody, a minibody, or a diabody.

4. The composition of claim 2, wherein the monoclonal antibody is a chimeric, humanized, or human antibody.

5. The composition of claim 1, wherein the antigen-binding polypeptide or protein has a molecular mass of at least 90 kDa.

6. The composition of claim 1, wherein the semifluorinated alkane is selected from F4H5, F4H6, F4H8, F6H4, F6H6, and F6H8.

7. The composition of claim 1, wherein the semifluorinated alkane is selected from F4H5 and F6H8.

8. The composition of claim 1, wherein the semifluorinated alkane is F6H10.

9. The composition of claim 1, wherein the composition consists essentially of the antigen-binding polypeptide or protein and the liquid vehicle, the liquid vehicle consisting of one or more semi-fluorinated alkanes selected from F4H5, F4H6, F4H8, F6H4, F6H6, F6H8, and F6H10.

10. The composition of claim 1, wherein the composition retains at least 85% of its initial antigen-binding activity during storage of 6 months at a temperature of between RT to 40° C.

11. The composition of claim 1, wherein the antigen-binding polypeptide or protein is at a concentration of at least 0.5 mg/mL.

12. The composition of claim 1, wherein the antigen-binding polypeptide or protein is an angiogenesis inhibitor, an anti-proliferative agent or a TNF inhibitor.

13. The composition of claim 2, wherein the semifluorinated alkane is selected from F4H5, F4H6, F4H8, F6H4, F6H6, and F6H8.

14. The composition of claim 13, wherein the composition consists essentially of the antigen-binding polypeptide or protein and the liquid vehicle, the liquid vehicle consisting of one or more semi-fluorinated alkanes selected from F4H5 and F6H8.

15. The composition of claim 13, wherein the composition consists essentially of the antigen-binding polypeptide or protein and the liquid vehicle, the liquid vehicle consisting of F6H10.

16. The composition according to claim 1, wherein the antigen-binding polypeptide or protein is not dissolved in the SFA.

17. The composition according to claim 1, wherein the composition is formulated for topical administration to the eye, ear or nose or for parenteral administration.

18. The composition according to claim 1, wherein the antigen-binding polypeptide or protein is suspended as solid particles in the liquid vehicle.

19. The composition according to claim 18, wherein the solid particles of the antigen-binding polypeptide or protein are prepared by lyophilization or spray-drying of an aqueous or non-aqueous solution comprising the antigen-binding polypeptide or protein.

20. The composition according to claim 18, wherein the particle size of the suspended antigen-binding polypeptide or protein is adjusted before or after the particles are combined with the liquid vehicle.

\* \* \* \* \*